(12) United States Patent
Gunderson (10) Patent No.: US 8,152,818 B2
(45) Date of Patent: Apr. 10, 2012

(54) MEDICAL DEVICE DELIVERY SYSTEMS

(75) Inventor: Richard C. Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 567 days.

(21) Appl. No.: 11/838,495

(22) Filed: Aug. 14, 2007

(65) Prior Publication Data

US 2007/0282420 A1   Dec. 6, 2007

Related U.S. Application Data

(62) Division of application No. 10/753,715, filed on Jan. 8, 2004, now abandoned.

(51) Int. Cl.
*A61F 2/84* (2006.01)
(52) U.S. Cl. ........................ 606/108; 623/1.11; 623/1.23
(58) Field of Classification Search .................. 606/108; 623/1.11, 1.12, 1.23; 604/43, 264, 4.01
See application file for complete search history.

(56) References Cited

U.S. PATENT DOCUMENTS

| | | | |
|---|---|---|---|
| 3,613,684 A | 10/1971 | Sheridan | |
| 5,346,471 A | 9/1994 | Raulerson | |
| 5,695,499 A | 12/1997 | Helgerson et al. | |
| 5,733,267 A | 3/1998 | Del Toro | |
| 5,755,777 A | 5/1998 | Chuter | |
| 5,772,669 A | 6/1998 | Vrba | |
| 5,830,181 A | 11/1998 | Thornton | |
| 5,843,090 A | 12/1998 | Schuetz | |
| 5,882,347 A | 3/1999 | Mouris-Laan et al. | |
| 5,891,154 A | 4/1999 | Loeffler | |
| 5,906,619 A | 5/1999 | Olson et al. | |
| 5,954,764 A | 9/1999 | Parodi | |
| 5,980,483 A | 11/1999 | Dimitri | |
| 6,033,413 A | 3/2000 | Mikus et al. | |
| 6,120,522 A | 9/2000 | Vrba et al. | |
| 6,139,524 A | 10/2000 | Killion | |
| 6,254,609 B1 | 7/2001 | Vrba et al. | |
| 6,287,329 B1 | 9/2001 | Duerig et al. | |
| 6,322,586 B1 | 11/2001 | Monroe et al. | |
| 6,330,884 B1 * | 12/2001 | Kim | 128/898 |
| 6,331,184 B1 | 12/2001 | Abrams | |
| 6,342,066 B1 | 1/2002 | Toro et al. | |
| 6,355,060 B1 | 3/2002 | Lenker et al. | |
| 6,375,676 B1 | 4/2002 | Cox | |
| 6,398,802 B1 | 6/2002 | Yee | |
| 6,425,898 B1 | 7/2002 | Wilson et al. | |
| 6,514,228 B1 | 2/2003 | Hamilton et al. | |
| 6,576,006 B2 | 6/2003 | Limon et al. | |
| 6,589,251 B2 | 7/2003 | Yee et al. | |

(Continued)

FOREIGN PATENT DOCUMENTS

EP   0 775 470   5/1997

(Continued)

*Primary Examiner* — Ryan Severson
(74) *Attorney, Agent, or Firm* — Seager, Tufte & Wickhem, LLC (57) ABSTRACT

Medical device delivery systems, and related methods and components, are disclosed. In some embodiments, an implantable medical endoprosthesis delivery system includes a catheter, a sheath at least partially surrounding the catheter, and a tip coupled to a distal end portion of the catheter. The tip can cooperate with a distal end surface of the sheath to form a gap therebetween so that there is fluid communication between an interior region of the sheath and an exterior region of the sheath.

16 Claims, 10 Drawing Sheets

U.S. PATENT DOCUMENTS

| | | |
|---|---|---|
| 6,669,716 B1 | 12/2003 | Gilson et al. |
| 6,726,712 B1 | 4/2004 | Raeder-Devens et al. |
| 6,860,898 B2 | 3/2005 | Stack et al. |
| 6,939,352 B2 | 9/2005 | Buzzard et al. |
| 2001/0037141 A1* | 11/2001 | Yee et al. .................. 623/1.11 |
| 2002/0052641 A1 | 5/2002 | Monroe et al. |
| 2002/0058951 A1 | 5/2002 | Fiedler |
| 2002/0082550 A1 | 6/2002 | Hamilton et al. |
| 2002/0095203 A1 | 7/2002 | Thompson et al. |
| 2003/0163156 A1 | 8/2003 | Hebert et al. |

FOREIGN PATENT DOCUMENTS

| | | |
|---|---|---|
| EP | 1385450 | 3/2007 |
| WO | WO 02/056953 | 7/2002 |

* cited by examiner

MEDICAL DEVICE DELIVERY SYSTEMS

CROSS-REFERENCE TO RELATED APPLICATIONS

This application is a divisional of and claims priority to U.S. application Ser. No. 10/753,715, filed on Jan. 8, 2004 now abandoned.

TECHNICAL FIELD

The invention relates to medical device delivery systems, and related methods and components.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer tube surrounding an inner tube with a stent positioned therebetween. Generally, the operator of the system positions the distal portion within the lumen at a desired location (e.g., so that the stent is adjacent an occlusion). The operator can then retract the outer tube to allow the stent to engage the occlusion/lumen wall. Thereafter, the operator removes the distal portion of the system from the lumen. In many instances, a system can be designed to be flushed (e.g., with a saline solution) prior to delivery to a targeted site within the body. Such flushing can, for example, enhance the lubricity and/or deliverability of a system.

SUMMARY

The invention relates to medical device delivery systems, and related methods and components.

In one aspect, the invention features an implantable medical endoprosthesis delivery system. The system includes a catheter and a sheath that at least partially surrounds the catheter. The sheath has a proximal end, a distal end, and at least one orifice between the proximal and distal ends of the sheath. The catheter and the sheath are configured so that an implantable medical endoprosthesis can be disposed therebetween. The at least one orifice in the sheath is between the distal end of the sheath and a location in the sheath adjacent a proximal end of the implantable medical endoprosthesis.

In another aspect, the invention features a method of implanting an endoprosthesis in a lumen of a subject. The method includes disposing a system in the lumen of the subject. The system includes a catheter, a sheath that at least partially surrounds the catheter, and an implantable medical endoprosthesis between the catheter and the sheath. The sheath has a proximal end, a distal end, and at least one orifice between the proximal and distal ends of the sheath. The at least one orifice in the sheath is between the distal end of the sheath and a location in the sheath adjacent a proximal end of the implantable medical endoprosthesis. The method also includes at least partially retracting the sheath.

In a further aspect, the invention features an implantable medical endoprosthesis delivery system. The system includes a catheter and a sheath that at least partially surrounds the catheter. The sheath has a proximal end, a distal end, and at least one orifice that is at most about 100 millimeters from the distal end of the sheath. The catheter and the sheath are configured so that an implantable medical endoprosthesis can be disposed therebetween.

In one aspect, the invention features a method of implanting an endoprosthesis in a lumen of a subject. The method includes disposing a system in the lumen of the subject. The system includes a catheter, a sheath at least partially surrounding the catheter, and an implantable medical endoprosthesis between the catheter and the sheath. The sheath has a proximal end, a distal end, and at least one orifice that is at most about 100 millimeters from the distal end of the sheath. The method also includes at least partially retracting the sheath.

In another aspect, the invention features an implantable medical endoprosthesis delivery system. The system includes a catheter, a sheath and a tip. The sheath has a distal end with a shaped surface, and the sheath at least partially surrounds the catheter. The catheter and the sheath are configured so that an implantable medical endoprosthesis can be disposed therebetween. The tip is coupled to the distal end of the catheter, and the tip has a surface in partial contact with the shaped surface of the distal end of the sheath so that there is fluid communication between an interior region of the sheath and an exterior region of the sheath.

In a further aspect, the invention features a method of implanting an endoprosthesis in a lumen of a subject. The method includes disposing a system in the lumen of the subject. The system includes a catheter, a sheath and a tip. The sheath has a distal end with a shaped surface, and the sheath at least partially surrounds the catheter. The system also includes an implantable medical endoprosthesis between the catheter and the sheath. The tip is coupled to the distal end of the catheter, and the tip has a surface in partial contact with the shaped surface of the distal end of the sheath so that there is fluid communication between an interior region of the sheath and an exterior region of the sheath. The method further includes at least partially retracting the sheath.

In one aspect, the invention features an implantable medical endoprosthesis delivery system. The system includes a catheter, a sheath and a tip. The sheath at least partially surrounds the catheter. The catheter and the sheath are configured so that an implantable medical endoprosthesis can be disposed therebetween. The tip is coupled to the distal end of the catheter, and the tip has a shaped surface in partial contact with the surface of the distal end of the sheath so that there is fluid communication between an interior region of the sheath and an exterior region of the sheath.

In another aspect, the invention features a method of implanting an endoprosthesis in a lumen of a subject. The method includes disposing a system in the lumen of the subject. The system includes a catheter, a sheath and a tip. The sheath at least partially surrounds the catheter. An implantable medical endoprosthesis is disposed between the catheter and the sheath. The tip is coupled to the distal end of the catheter, and the tip has a shaped surface in partial contact with the surface of the distal end of the sheath so that there is fluid communication between an interior region of the sheath and an exterior region of the sheath. The method further includes at least partially retracting the sheath.

In a further aspect, the invention features an implantable medical endoprosthesis delivery system. The system includes a catheter, a sheath and a tip. The sheath has a distal end with a surface, and the sheath at least partially surrounds the catheter so that an implantable medical endoprosthesis can be disposed therebetween. The tip is coupled to the distal end of the catheter. At least one slot of material is disposed between the surface of the tip and the surface of the distal end of the sheath so that there is fluid communication between an interior region of the sheath and an exterior region of the sheath.

In one aspect, the invention features a method of implanting an endoprosthesis in a lumen of a subject. The method includes disposing a system in the lumen of the subject. The system includes a catheter and a sheath. An implantable medical endoprosthesis is disposed between the catheter and the sheath. The system also includes a tip that is coupled to the distal end of the catheter. The system further includes at least one slot of material that is disposed between the surface of the tip and the surface of the distal end of the sheath so that there is fluid communication between an interior region of the sheath and an exterior region of the sheath. The method further includes at least partially retracting the sheath.

In another aspect, the invention features a method that includes passing a fluid from an interior of a sheath of an implantable medical endoprosthesis delivery system to an exterior of the sheath through an orifice in the sheath. The system includes the sheath and a catheter that is at least partially surrounded by the sheath, so that an implantable medical endoprosthesis can be disposed between the catheter and the sheath in a location. The orifice is between a distal end of a sheath and a location in the sheath that is adjacent a proximal end of the location for the implantable medical endoprosthesis.

In a further aspect, the invention features a method that includes passing a fluid from an interior of a sheath of an implantable medical endoprosthesis delivery system to an exterior of the sheath through an orifice in the sheath. The system includes the sheath and a catheter that is at least partially surrounded by the sheath so that an implantable medical endoprosthesis can be disposed between the catheter and the sheath. The orifice in the sheath is at most about 100 millimeters from the distal end of the sheath.

In one aspect, the invention features a method that includes passing a fluid from an interior of a sheath of an implantable medical endoprosthesis delivery system to an exterior of the sheath. The system includes the sheath, a catheter at least partially surrounded by the sheath so that an implantable medical endoprosthesis can be disposed between the catheter and the sheath, and a tip coupled to a distal end of the catheter. The tip has a surface that is in partial contact with a shaped surface of a distal end of the sheath so that there is fluid communication between an interior region of the sheath and an exterior region of the sheath.

In another aspect, the invention features a method that includes passing a fluid from an interior of a sheath of an implantable medical endoprosthesis delivery system to an exterior of the sheath. The system includes the sheath, a catheter at least partially surrounded by the sheath so that an implantable medical endoprosthesis can be disposed between the catheter and the sheath, and a tip coupled to a distal end of the catheter. The tip has a shaped surface that is in partial contact with a surface of a distal end of the sheath so that there is fluid communication between an interior region of the sheath and an exterior region of the sheath.

In a further aspect, the invention features a method that includes passing a fluid from an interior of a sheath of an implantable medical endoprosthesis delivery system to an exterior of the sheath. The system includes the sheath, and a catheter at least partially surrounded by the sheath so that an implantable medical endoprosthesis can be disposed between the catheter and the sheath. The system also includes a tip that is coupled to a distal end of the catheter and that has a surface. The system filter includes at least one slot of material that is disposed between the surface of the tip and a surface of a distal end of the sheath so that there is fluid communication between an interior region of the sheath and an exterior region of the sheath.

In one aspect, the invention features a guide catheter that has a proximal end, a distal end, and at least one orifice between the proximal and distal ends of the guide catheter. The at least one orifice is at most about 100 millimeters from the distal end of the guide catheter.

Embodiments can include one or more of the following features.

The system can be configured so that, when the implantable medical endoprosthesis is disposed between the catheter and the sheath, the system can deliver the implantable medical endoprosthesis into a lumen of a subject.

In some embodiments, a sheath can include a plurality of orifices, with at least some of the orifices being between the distal end of the sheath and the location in the sheath adjacent the proximal end of the implantable medical endoprosthesis.

The implantable medical endoprosthesis can be, for example, a stent, a stent-graft or a vena cava filter.

In some embodiments, the implantable medical endoprosthesis can have at least one strut with a maximum dimension that is greater than the maximum dimension of the at least one orifice.

In certain embodiments, the maximum dimension of the at least one orifice is about 0.02 inch or less (e.g., about 0.01 inch or less).

A sheath can include multiple layers. One or more of the layers can be a support material (e.g., a mesh, a wire, a braided material). The implantable medical endoprosthesis can have at least one strut with a maximum dimension that is smaller than a maximum dimension of the at least one orifice in the sheath.

The system can further include the implantable medical endoprosthesis between the catheter and the sheath.

The implantable medical endoprosthesis can be a self-expanding implantable medical endoprosthesis. The implantable medical endoprosthesis can expand as the sheath is at least partially retracted.

The implantable medical endoprosthesis can be a balloon expandable implantable medical endoprosthesis. The catheter can include an inflatable member, and the method can further include, after at least partially retracting the sheath, inflating the inflatable member to expand the implantable medical endoprosthesis.

The system can further include a tip coupled to a distal end of the catheter.

The at least one orifice can be at most about 100 millimeters from the distal end of the sheath, and/or the at least one orifice can be at least about one millimeter from the distal end of the sheath. The system can include a plurality of orifices, and at least some of the orifices can be at most about 100 millimeters from the distal end of the sheath.

A shaped surface can be, for example, a scalloped surface or a serrated surface.

In some embodiments, the system includes a plurality of slots of material.

The at least one slot of material can be integral with the tip.

The at least one slot of material can extend outwardly from the tip.

The at least one slot of material can be integral with the sheath.

The at least one slot of material can extend inwardly from the sheath.

A portion of the sheath can surround (e.g., can be line fit to) a portion of the at least one slot of material.

Passing a fluid from an interior of a sheath of an implantable medical endoprosthesis delivery system to an exterior of the sheath (e.g., through an orifice in the sheath) can remove substantially all gas from the interior of the sheath.

Embodiments can include one or more of the following advantages.

In certain embodiments, a system can be lubricated and/or purged (e.g., using a saline solution) prior to use without undesired separation of the sheath from the tip. For example, in some embodiments, a system can be lubricated and/or purged (e.g., using a saline solution) without the sheath flaring outwardly.

In some embodiments, a system can be efficiently and/or effectively flushed (e.g., to lubricate the system). For example, in certain embodiments, a system can be thoroughly flushed using a relatively low number of flushing cycles.

In certain embodiments, a system can exhibit enhanced medical device deployment performance. For example, by being properly lubricated, the sheath can be retracted in a relatively uniform manner, resulting in relatively high control over the positioning of the medical device (e.g., within the lumen of the subject).

In certain embodiments, the systems can be flushed (e.g., prior to use in vivo) to purge or aspirate the systems of substantially all gas (e.g., air pockets and/or air bubbles).

Features and advantages of the invention are in the description, drawings, and claims.

DETAILED DESCRIPTION

In general, the delivery systems are designed to provide fluid communication between the interior and exterior regions of the sheath, particularly toward the distal region of the sheath. It is believed that such systems can reduce the likelihood that the sheath will undergo undesired separation from the tip during flushing of the system. For example, allowing fluid communication between the interior and exterior regions of the sheath can reduce gas build up in the interior region of the sheath during flushing. Certain embodiments of the systems are disclosed below.

Figure 1A:
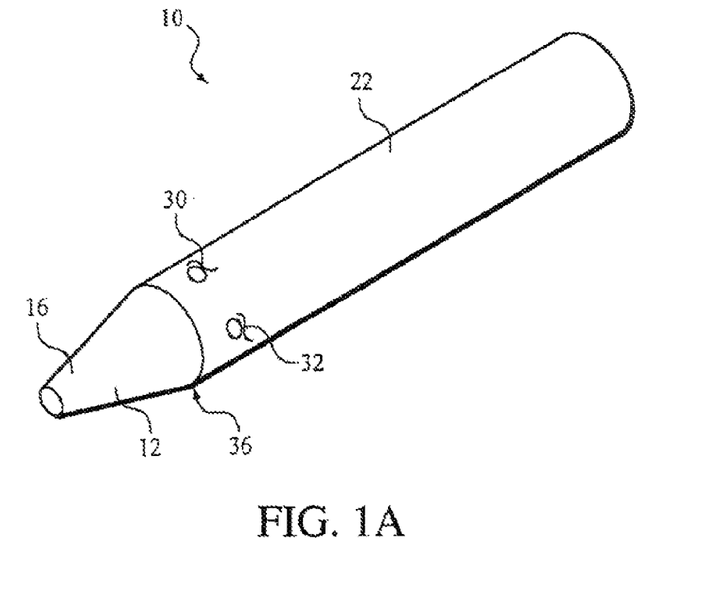
FIG. 1A is a perspective view of an embodiment of a stent delivery system.
Figure 1B:
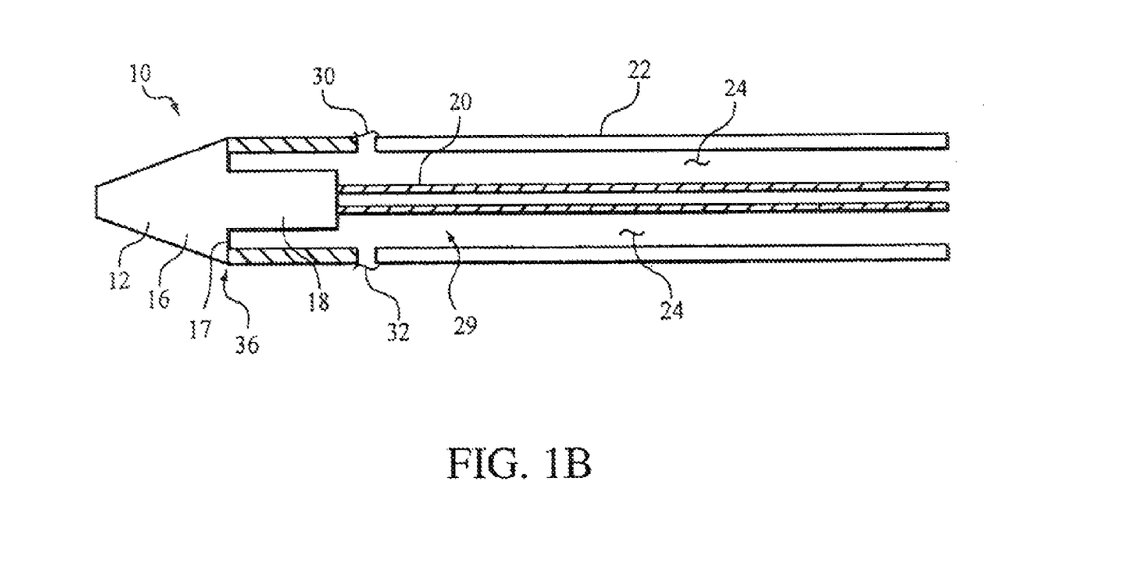
FIG. 1B is a cross-sectional view of the stent delivery system of FIG. 1A.
Figure 1C:
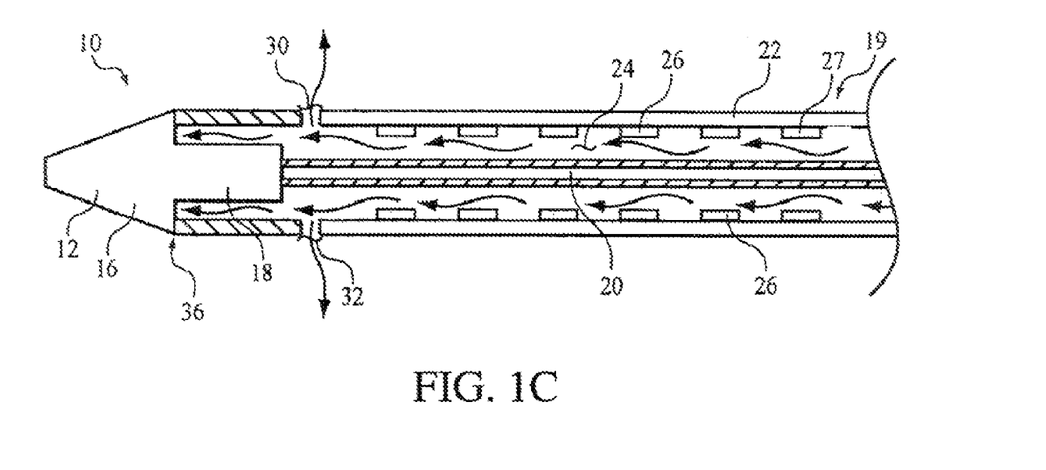
FIG. 1C is an illustration of an embodiment of a method of flushing the stent delivery system of FIGS. 1A and 1B.

In some embodiments, fluid communication between the interior and exterior regions of the sheath is provided by one or more holes in the sheath. For example, FIGS. 1A and 1B show a stent delivery system 10 that includes a distal tip 12, a catheter 20 and a sheath 22 having holes 30 and 32. Sheath 22 surrounds catheter 20 so that a stent 26 (shown in FIG. 1C) can be disposed in a space 24 between catheter 20 and sheath 22. Distal tip 12 includes a head portion 16 and a proximal portion 18. Head portion 16 includes a ledge 17 that is in contact with a distal end 36 of sheath 22. As shown in FIG. 1C, when system 10 is flushed with a fluid (e.g., a saline solution), the fluid (depicted as arrows) travels through space 24 and exits system 10 through holes 30 and 32.

In general, holes 30 and 32 are positioned toward distal end 36 of sheath 22. In some embodiments, holes 30 and 32 are located between distal end 36 of sheath 22 and a location 19 in sheath 22 that is adjacent a proximal end 27 of stent 26. In certain embodiments, holes 30 and 32 are located at least about one millimeter (e.g., at least about two millimeters, at least about five millimeters, at least about 10 millimeters, at least about 15 millimeters, at least about 20 millimeters) from distal end 36 of sheath 22, and/or at most about 100 millimeters (e.g., at most about 90 millimeters, at most about 80 millimeters, at most about 70 millimeters, at most about 60 millimeters) from distal end 36 of sheath 22.

Generally, holes 30 and 32 can be dimensioned as desired. In certain embodiments, holes 30 and/or 32 have a maximum dimension (e.g., a diameter) of at most about 0.05 inch (e.g., at most about 0.03 inch, at most about 0.02 inch, at most about 0.01 inch, at most about 0.005 inch). In some embodiments, holes 30 and/or 32 are dimensioned to a component (e.g., a strut) of stent 26 from protruding through the holes 30 and 32. In such embodiments, holes 30 and 32 can have, for example, a maximum dimension that is smaller than a maximum dimension of the component (e.g., the strut) of stent 26. As an example, a coronary stent delivery system (e.g., having struts with dimensions of 0.004 inch×0.004 inch) can include a sheath that has one or more holes with a maximum dimension of, for example, 0.003 inch (e.g., one or more square holes with dimensions of 0.003 inch×0.003 inch). As another example, a peripheral stent delivery system (e.g., having struts with dimensions of 0.008 inch×0.008 inch) can include a sheath that has, one or more holes with a maximum dimension of, for example, 0.007 inch (e.g., one or more square holes with dimensions of 0.007 inch×0.007 inch).

Figure 2:
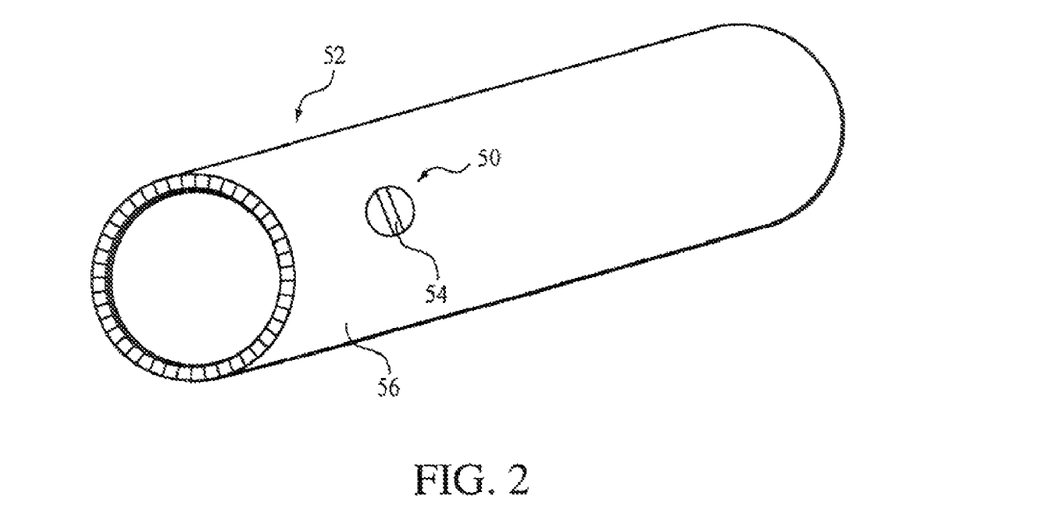
FIG. 2 is a perspective view of an embodiment of a stent delivery system.
Figure 3:
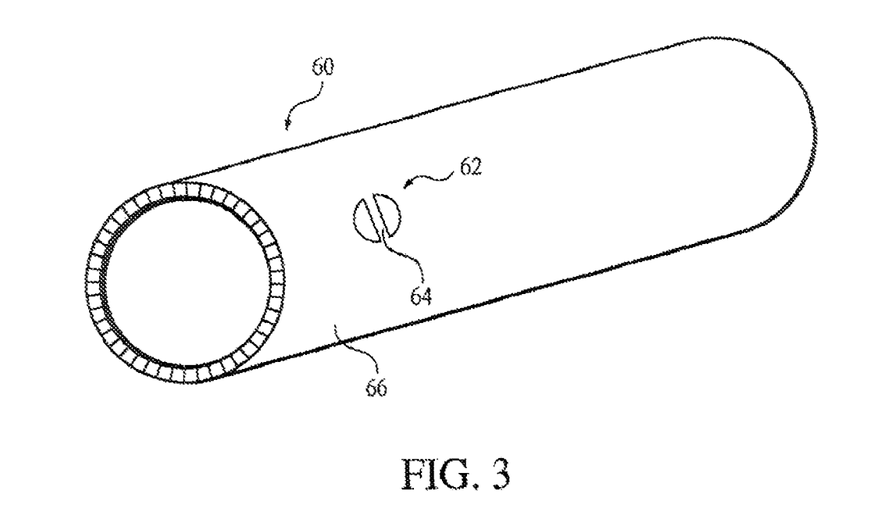
FIG. 3 is a perspective view of an embodiment of a stent delivery system.

In some embodiments, a sheath can have one or more holes that are partially covered by a strip of material across the hole(s). For example, FIG. 2 shows a sheath 52 with an opening 50 (e.g., a hole) having a strip of material 54 across hole 50. Typically, strip 54 is attached (e.g., adhesive-bonded) to a wall 56 of sheath 52. Strip 54 can be formed of the same material as sheath 50 or a different material from sheath 50. Examples of materials from which strip 54 can be formed include polymers (e.g., PEBAX, Hytrel, Arnitel, Nylon) and/or metals (e.g., stainless steel, platinum, gold, tantalum). In certain embodiments the strip of material can be integral with (e.g., formed of the same material as) the sheath. For example, FIG. 3 shows a sheath 60 with an opening 62 is partially covered by a strip of material 64 that is integrally formed with a wall 66 of sheath 60. In embodiments in which a hole in a sheath is partially covered by a strip of material, the hole can have a maximum dimension (e.g., a maximum diameter) of at least about 0.020 inch (e.g., at least about 0.025 inch, at least about 0.030 inch) and/or at most about 0.060 inch (e.g., at most about 0.050 inch, at most about 0.040 inch).

Figure 4:
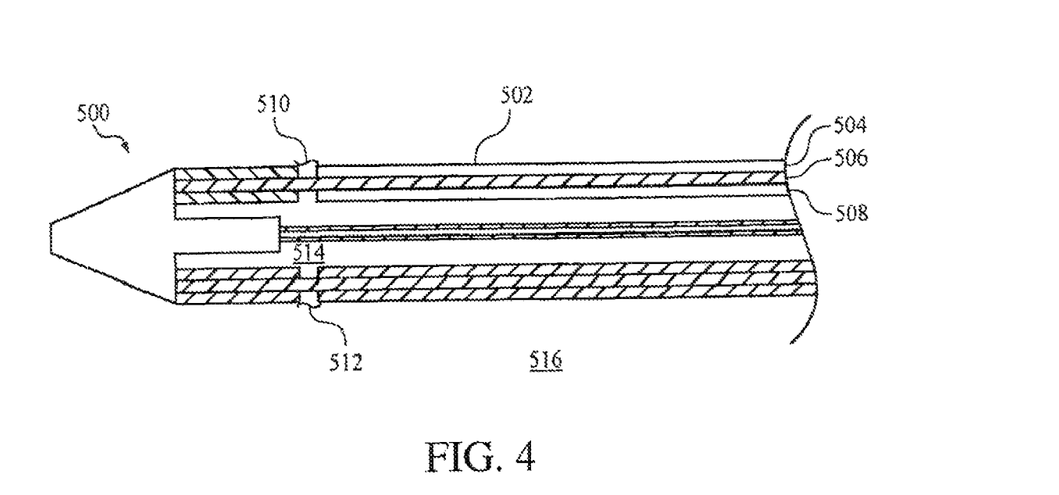
FIG. 4 is a cross-sectional view of an embodiment of a stent delivery system.

In certain embodiments, the sheath can include multiple layers of material. In such embodiments, one or more of the layers can be formed of an open support material (e.g., a mesh, a wire, a braided, material). Typically, the support material is covered by one or more of the other layers of material. FIG. 4 shows a stent delivery system 500 with a sheath 502 that includes an outer layer (e.g., a PEBAX layer) 504, a middle layer (e.g., a metal braided layer) 506, and an inner layer (e.g., a PTFE layer) 508. Sheath 502 includes holes 510 and 512 that extend in layers 504 and 508 but not in layer 506. Because of the open nature of layer 506, there is fluid communication between an interior region 514 of sheath 502 and an exterior region 516 of sheath 502 via holes 510 and 512.

In general, a hole can be formed in a sheath by any of a number of different methods. Such methods include, for example, mechanical drilling, punching, cutting, and laser drilling/ablation, and chemical etching.

Figure 5A:
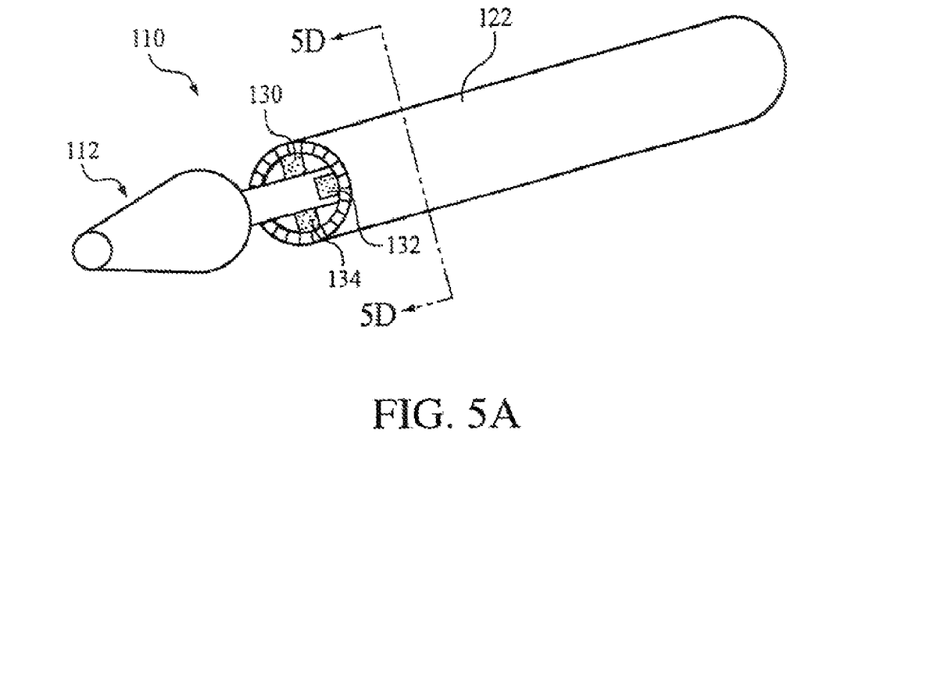
FIG. 5A is a perspective view of an embodiment of a stent delivery system.
Figure 5B:
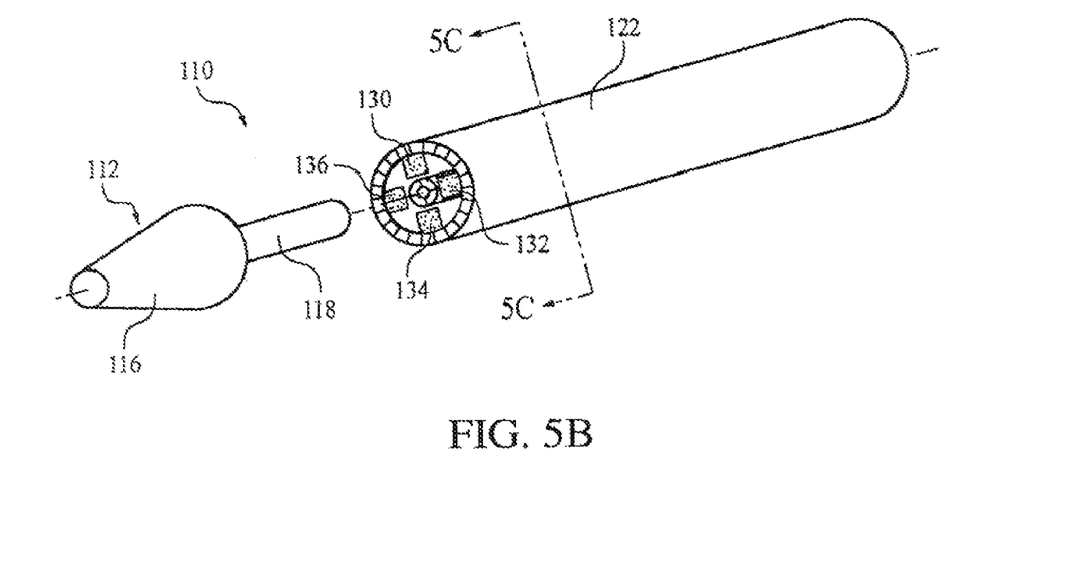
FIG. 5B is an exploded view of the stent delivery system of FIG. 5A.
Figure 5C:
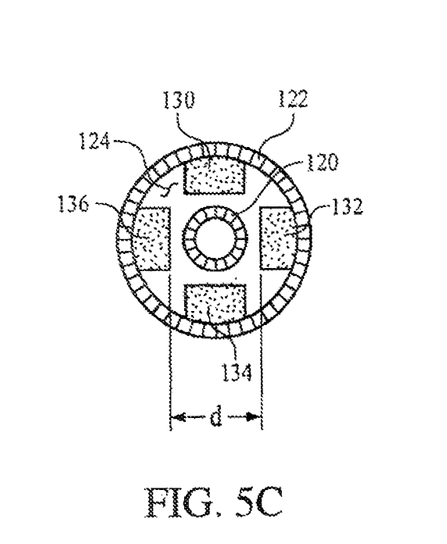
FIG. 5C is a cross-sectional view of a component of the stent delivery system of FIG. 5B, taken along line 5C-5C.
Figure 5D:
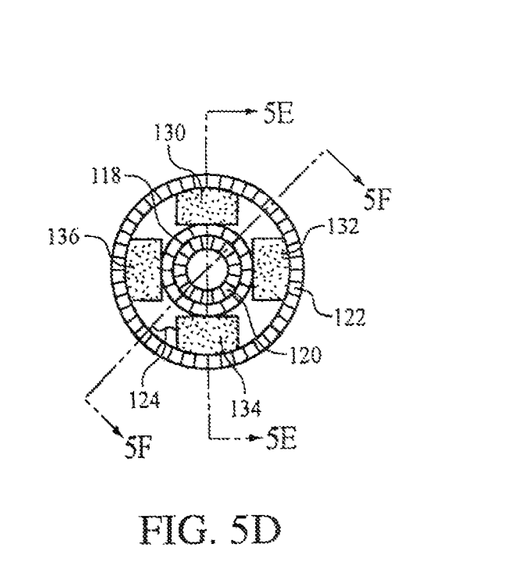
FIG. 5D is a cross-sectional view of the stent delivery system of FIG. 5A, taken along line 5D-5D.
Figure 5E:
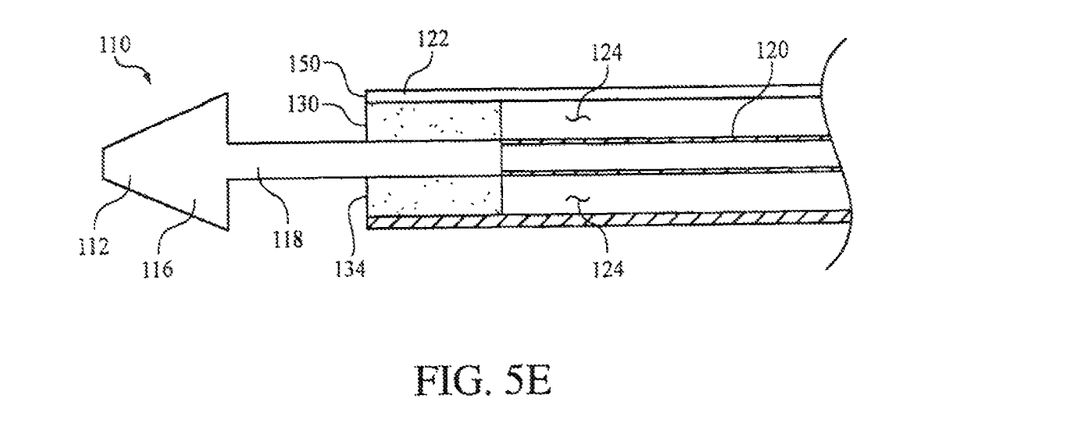
FIG. 5E is a cross-sectional view of the stent delivery system of FIG. 5D, taken along line 5E-5E.
Figure 5F:
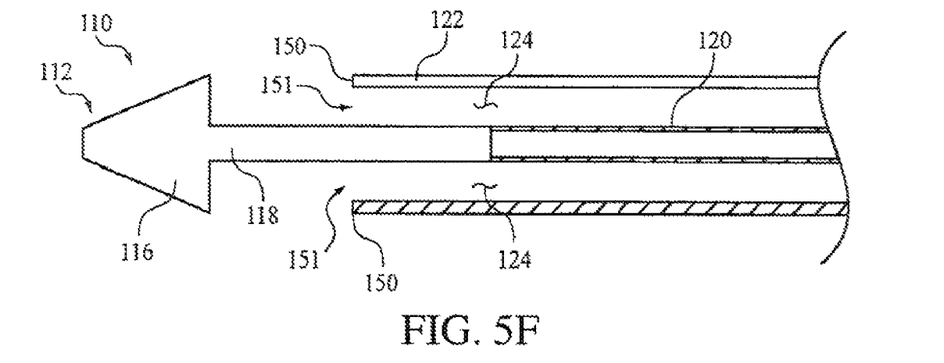
FIG. 5F is a cross-sectional view of the stent delivery system of FIG. 5D, taken along line 5F-5F.
Figure 5G:
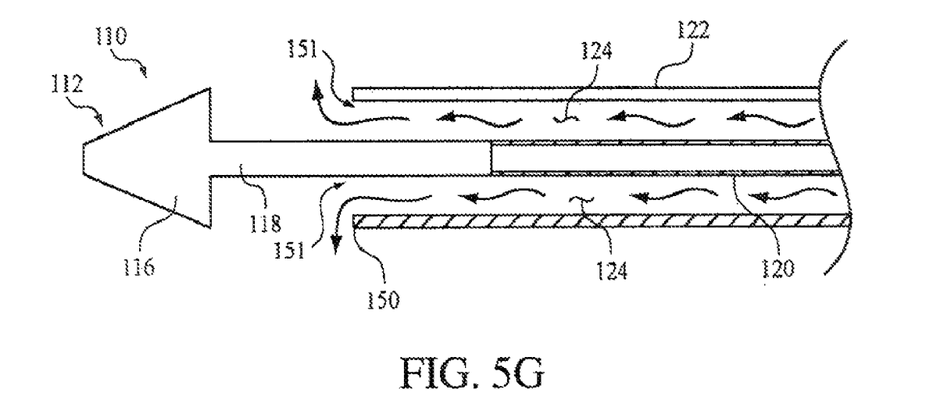
FIG. 5G is an illustration of an embodiment of a method of flushing the stent delivery system shown in FIG. 5F.
Figure 5H:
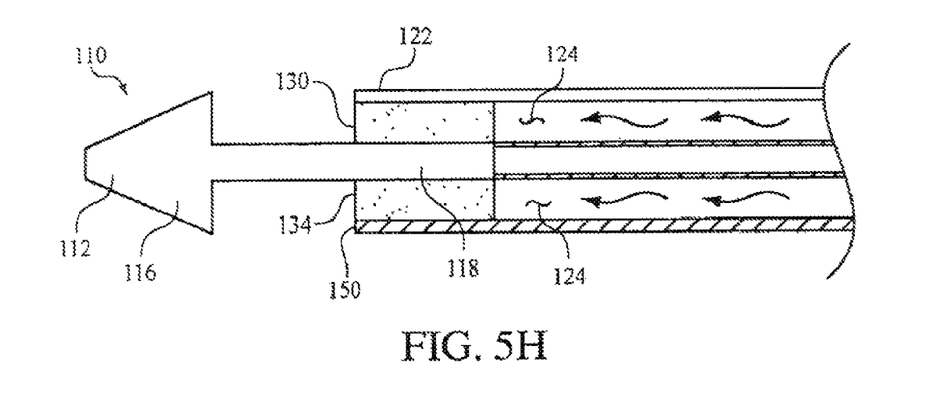
FIG. 5H is an illustration of an embodiment of a method of flushing the stent delivery system shown in FIG. 5E.
Figure 6A:
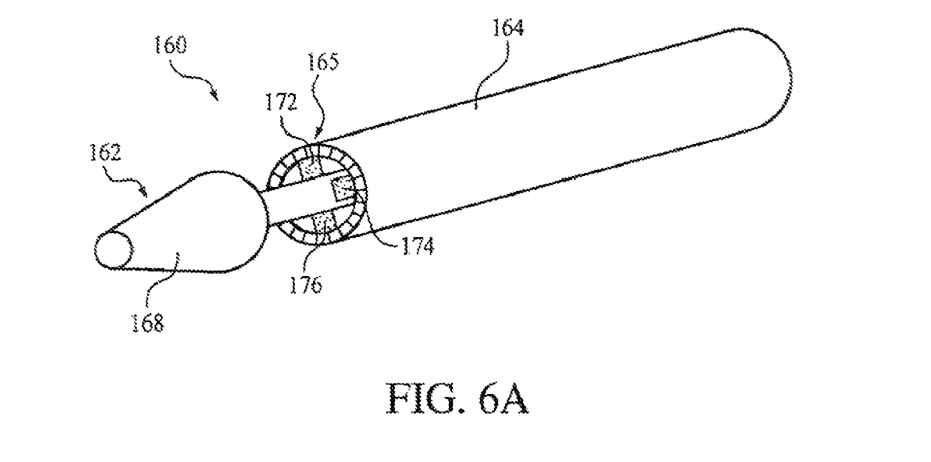
FIG. 6A is a perspective view of an embodiment of stent delivery system.
Figure 6B:
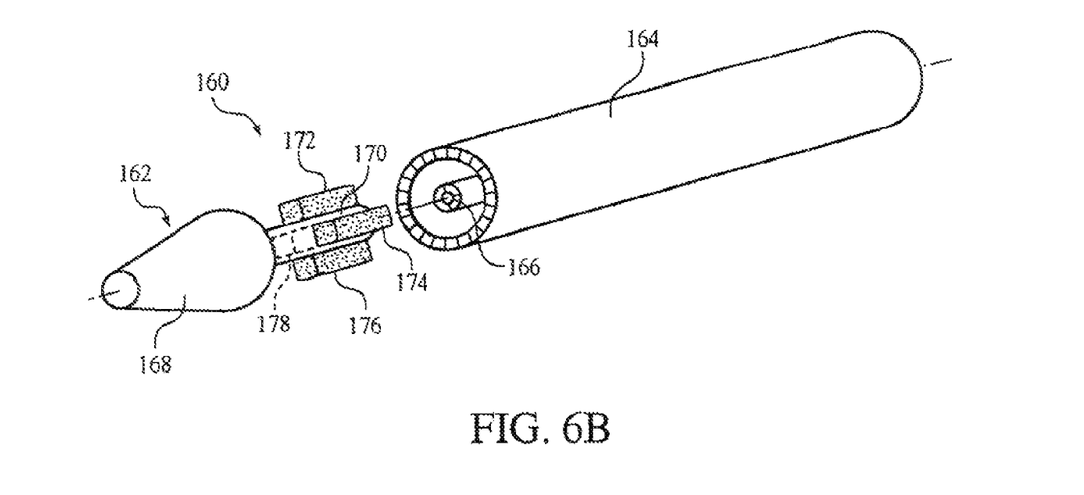
FIG. 6B is an exploded view of the stent delivery system of FIG. 6A.
Figure 6C:
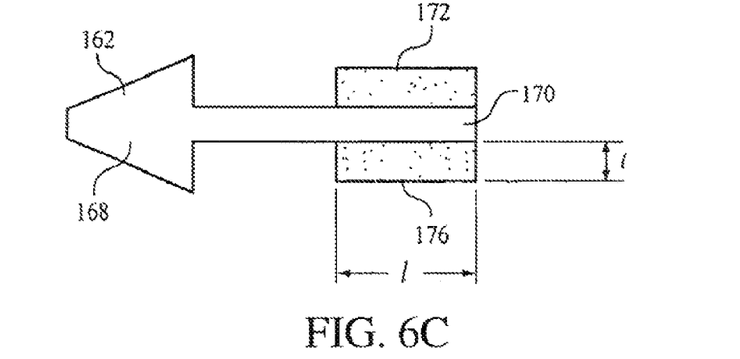
FIG. 6C is a side view of a distal tip of the stent delivery system of FIGS. 6A and 6B.
Figure 6D:
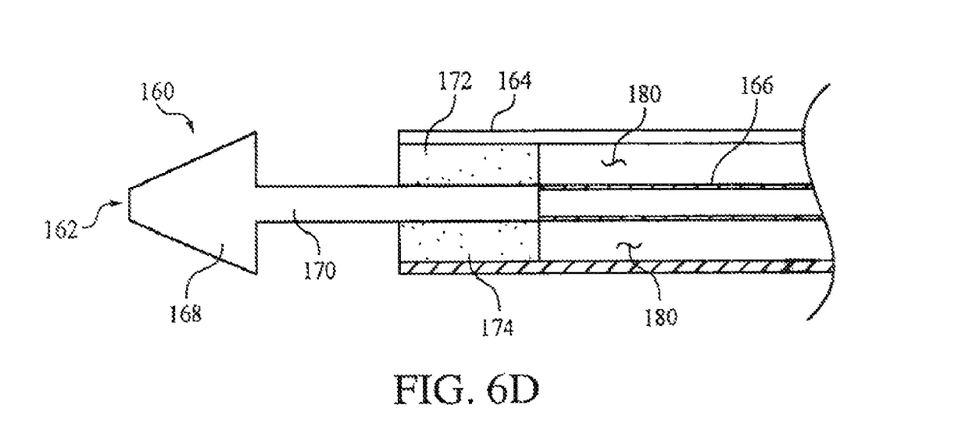
FIG. 6D is a side view of the stent delivery system of FIGS. 6A and 6B.
Figure 6E:
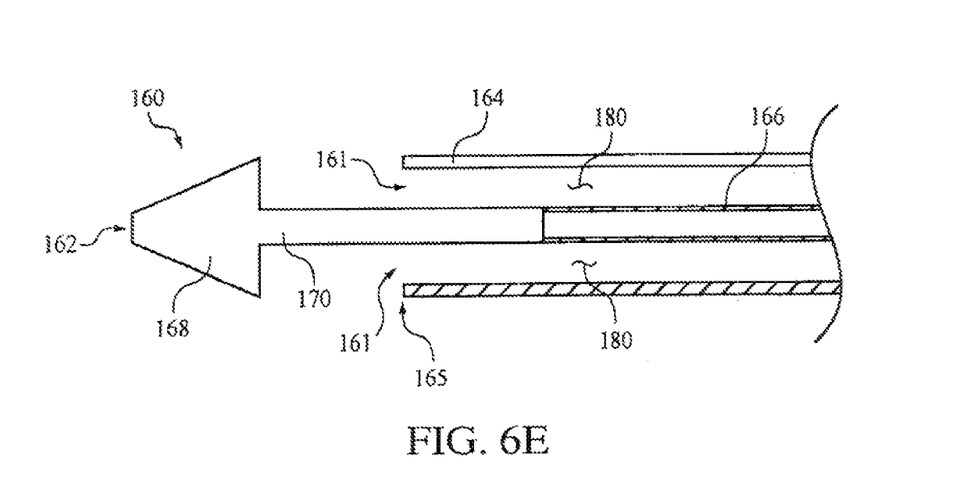
FIG. 6E is a side view of the stent delivery system of FIGS. 6A and 6B.

In some embodiments, fluid communication between the interior and exterior regions of the sheath is provided by disposing slots of material between the distal end of the sheath and the distal tip. For example, FIGS. 5A-5F show a stent delivery system 110 that includes a distal tip 112, a catheter 120, and a sheath 122 that partially surrounds catheter 120 so that an implantable medical endoprosthesis (e.g., a stent) can be disposed in a space 124 between catheter 120 and sheath 122. System 110 also includes a distal tip 112 with a head portion 116 that is integral with a proximal portion 118. Slots of material 130, 132, 134, and 136 are attached to sheath 122 and disposed between sheath 122 and portion 118 of distal tip 112. The outer diameter of portion 118 is about the same as distance "d" so that the slots and portion 118 form a line fit. Outlets 151 are located at a distal end 150 of sheath 122 where slots 130, 132, 134, and 136 are not present. As shown in FIGS. 5G and 5H (which correspond to the views of FIGS. 5F and 5E, respectively), a flushing fluid (depicted as arrows) can travel through space 124 between catheter 120 and sheath 122, and exit sheath 122 via openings 151. The line fit between the slots and portion 118 can prevent distal end 150 of sheath 122 from extending outwardly during flushing.

In some embodiments, the slots of material can be attached to the distal tip of a stent delivery system. For example, FIGS. 6A-6E show a stent delivery system 160 that includes a distal tip 162, a catheter 166, and a sheath 164 that partially surrounds catheter 166 so that an implantable medical endoprosthesis (e.g., a stent) can be disposed in a space 180 between catheter 166 and sheath 164. System 160 also includes a distal tip 162 with a head portion 168 that is integral with a proximal portion 170. Slots of material 172, 174, 176, and 178 are attached to portion 170. Outlets 161 are located at a distal end 165 of sheath 164 where slots 172, 174, 176, and 178 are not present. The slots and portion 170 are line fit, which can prevent distal end 165 of sheath 164 from extending outwardly during flushing.

In general, the dimensions of a slot of material can be selected as desired. In some embodiments, a slot of material can have a length "L" (shown in FIG. 6C) of at least about 0.050 inch (e.g., at least about 0.060 inch, at least about 0.070 inch) and/or at most about 0.100 inch (e.g., at most about 0.090 inch, at most about 0.080 inch). In certain embodiments, a slot of material can have a thickness "T" (shown in FIG. 6C) of at least about 0.015 inch (e.g., at least about 0.010 inch, at least about 0.005 inch) and/or at most about 0.020 inch (e.g., at most about 0.017 inch, at most about 0.015 inch).

The slots of material can be formed of, for example, a polymer, a metal, or a combination of these materials. Examples of polymers include PEBAX, Arnitel, Hytrel, and combinations of these materials. In some embodiments, one or more polymers can include a filler (e.g., a radiopaque material). Examples of metals include stainless steel, platinum, gold, tantalum, and MP35N (a nickel-cobalt-chromium-molybdenum alloy). In some embodiments, the slots of material can be formed of the same material as the distal tip and/or the sheath.

Generally, a slot of material can be attached to a tip or sheath using any desired method. Examples of methods include adhesive bonding and/or heat bonding (e.g., using laser heating, using RF heating). In some embodiments, a slot of material can be integrally formed (e.g., extruded or molded) with the sheath or distal tip.

Figure 7A:
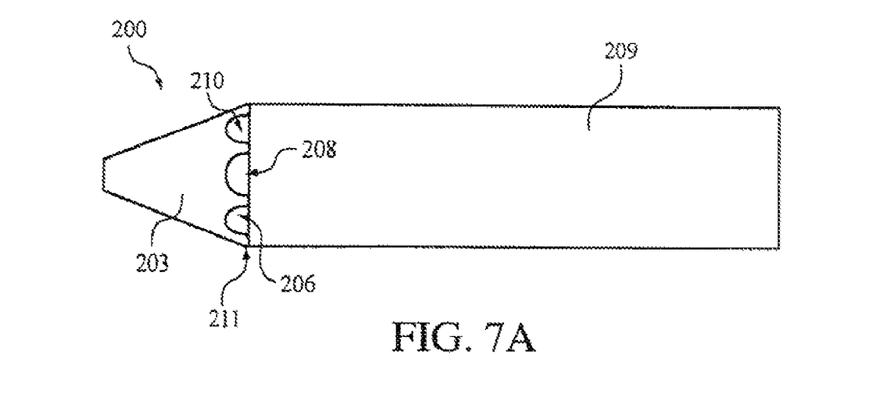
FIG. 7A is a side view of an embodiment of a stent delivery system.
Figure 7B:
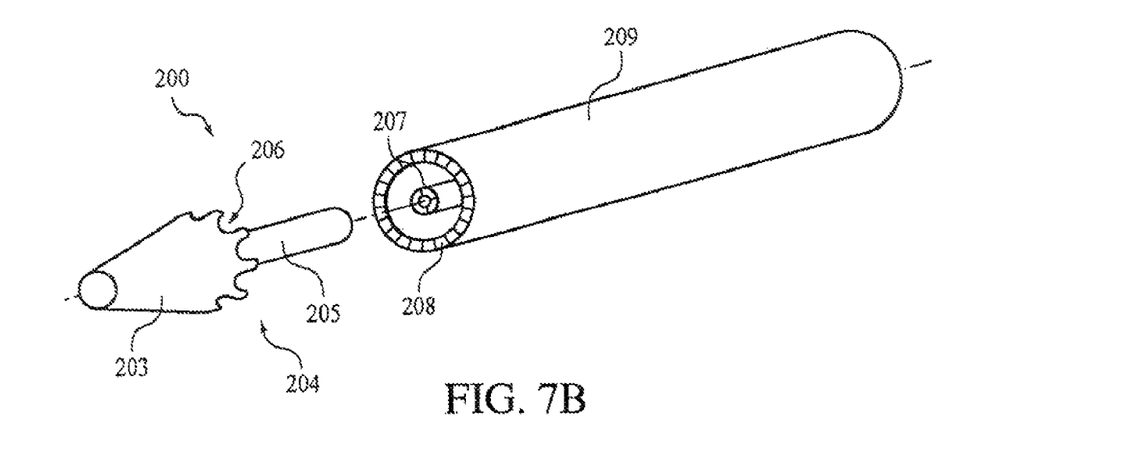
FIG. 7B is an exploded view of the stent delivery system of FIG. 7A.
Figure 7C:
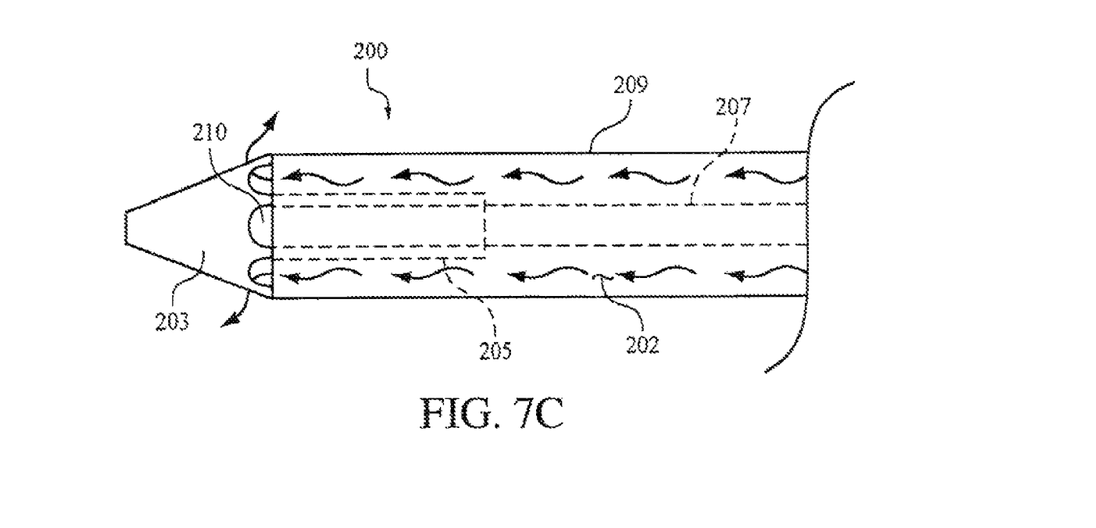
FIG. 7C is an illustration of an embodiment of a method of flushing the stent delivery system of FIGS. 7A and 7B.

In certain embodiments, fluid communication between the interior and exterior regions of the sheath is provided by shaping a surface of the tip and/or the surface of the distal end of the sheath. For example, FIGS. 7A-7C show a stent delivery system 200 that includes a distal tip 204, a catheter 207, and a sheath 209 that partially surrounds catheter 207 so that an implantable medical endoprosthesis (e.g., a stent) can be disposed in a space 202 between catheter 207 and sheath 209. Distal tip 204 has a head portion 203 and a proximal portion 205. Head portion 203 has a scalloped (shaped) surface 206 so that, when system 200 is assembled, portions of surface 206 contact a surface 208 of a distal end 211 of sheath 209, defining gaps 210 between surface 208 and the portions of surface 206 that do not contact surface 208. As shown in FIG. 7C, when a flushing fluid (depicted as arrows) travels through space 202, the fluid can travel from space 202 to the exterior of sheath 209 via gaps 210. The presence of gaps 210 can prevent distal end 211 of sheath 209 from extending outwardly during flushing.

While a system has been shown in which a surface of the tip has a scalloped shape, surfaces with other shapes can also be used. For example, the surface of the tip can be a serrated surface, a wavy surface, a pronged surface, or a surface having other types of protrusions (e.g., square protrusions, elliptical protrusions).

Figure 8A:
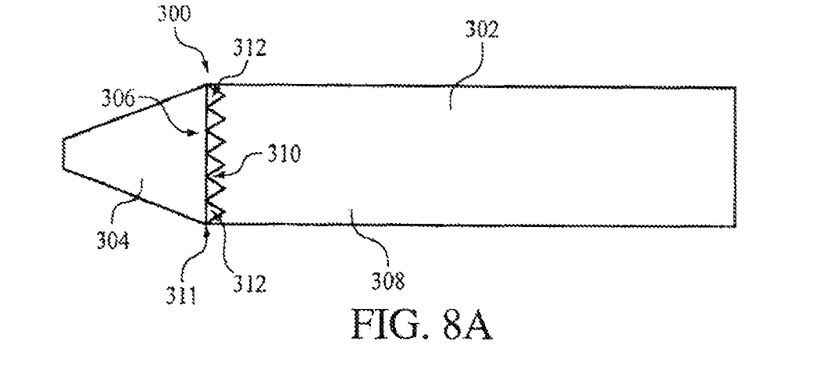
FIG. 8A is a side view of an embodiment of a stent delivery system.
Figure 8B:
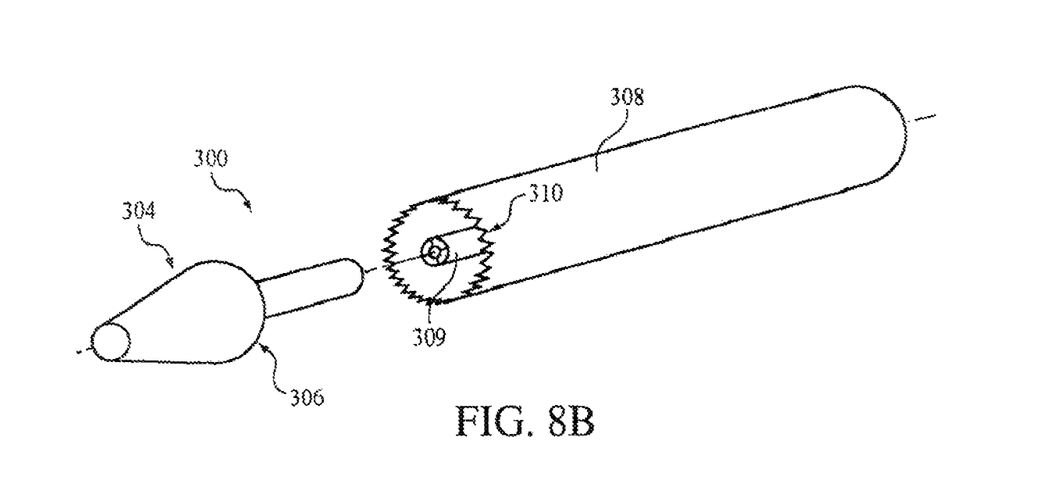
FIG. 8B is an exploded view of the stent delivery system of FIG. 8A.
Figure 8C:
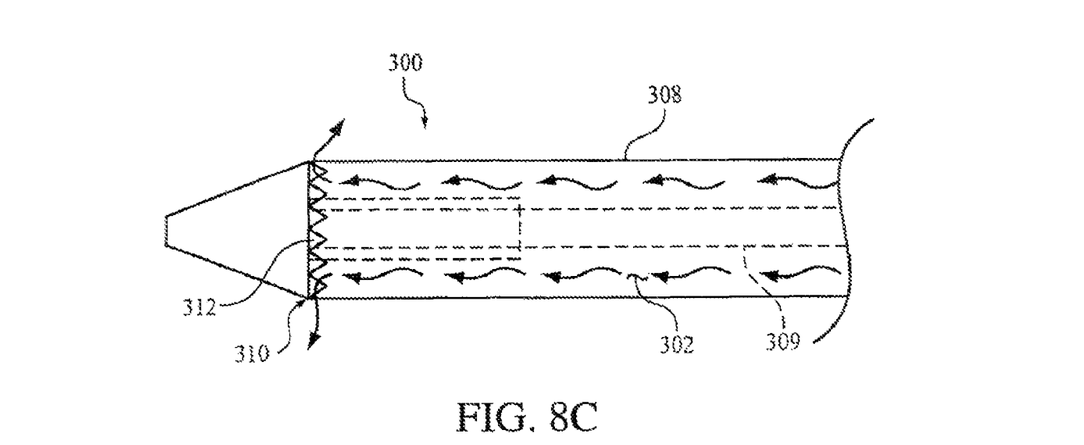
FIG. 8C is an illustration of an embodiment of a method of flushing the stent delivery system of FIGS. 8A and 8B.

In some embodiments, the surface of the distal end of the sheath, rather than a surface of the tip, can be shaped. For example, FIGS. 8A and 8B. show a stent delivery system 300 that includes a distal tip 304, a catheter 309, and a sheath 308 that partially surrounds catheter 309 so that an implantable medical endoprosthesis (e.g., a stent) can be disposed in a space 302 between catheter 309 and sheath 308. Sheath 308 has a distal end 311 with a serrated (shaped) surface 310 so that, when system 300 is assembled, portions of surface 310 contact a surface 306 of tip 304, defining gaps 312 between surface 306 and the portions of surface 310 that do not contact surface 306. As shown in FIG. 8C, when a flushing fluid (depicted as arrows) travels through space 302, the fluid can travel from space 302 to the exterior of sheath 308 via gaps 310. The presence of gaps 310 can prevent distal end 311 of sheath 209 from extending outwardly during flushing.

The surface of a tip and/or a sheath can generally be formed using any desired method. Examples of methods include cutting, heating, and laser-drilling a non-shaped (flat) surface. In some embodiments, a shaped surface can be molded and/or extruded as part of a sheath and/or distal tip. In certain embodiments, a protrusion can be attached to a non-shaped (flat) surface to provide a shaped surface.

The distal tip in stent delivery system is typically formed of a polymer. Alternatively or additionally, the sheath in a stent delivery system can be made of, for example, a polymer. Examples of polymers include the PEBAX family of polymers, silicones, thermoplastic polymers, thermoset polymers, Hytrel, Arnitel, PEEK (polyetheretherketone), and HDPE (high density polyethylene).

The catheter in a stent delivery system can be made of, for example, PEBAX, Hytrel, Arnitel, PEEK, and/or HDPE.

While certain embodiments have been described, the invention is not so limited.

As an example, while embodiments have been described in which a sheath includes two holes, in some embodiments, a sheath can include more or fewer than two holes. For example, a sheath can include one hole or three or more holes (e.g., four holes, five holes, six holes, seven holes, eight holes, nine holes, ten holes).

As another example, while embodiments have been described in which the holes in a sheath have had the same shape and/or size, in certain embodiments, at least some of the holes can have different shapes and/or sizes from each other.

As a further example, while embodiments have been described in which the holes in a sheath are all substantially the same distance from the distal end of the sheath, in some embodiments, at least some of the holes can be located at different distances from the distal end of the sheath.

As another example, while embodiments have been described in which the holes in the sheath are circular, in certain embodiments, at least some of the holes in a sheath can be noncircular (e.g., rectangular, square, triangular, elliptical).

As an additional example, in some embodiments, a hole in a sheath can be partially covered by multiple (e.g., two, three, four, five) strips of material.

As a further example, while rectangular slots have been described, slots of other shapes (e.g., cubic, cylindrical, spherical) can also be used.

As a farther example, while systems have been described that include four slots of material, in some embodiments, the number of slots can be greater than four or less than four. For example, a system can include one slot, two slots, three slots, five slots, six slots, seven slots, eight slots, nine slots, ten slots. In embodiments in which a stent delivery system includes multiple slots of material, the slots can all have the same size and/or shape, or can have different sizes and/or shapes.

As an additional example, both the surface of the distal end of the sheath and a surface of the distal tip can be shaped.

As another example, while systems have been described for delivering stents, in some embodiments, the systems can be used to deliver different implantable medical endoprostheses. In some embodiments, the system can be a stent-graft delivery system, In certain embodiments, the system can be a vena cava filter delivery system.

As described above, in some embodiments, the sheath can include one layer of material or three layers of material. However, in certain embodiments, the sheath can include a different number of layers of material (e.g., two layers of material, four layers of material, five layers of material). In embodiments in which the sheath is multilayered, the layers can be the same as, or different from, each other. In some cases, one or more of the layers in a sheath can be a support (e.g., mesh, wire, braided material) layer. In embodiments in which the sheath is multilayered, one or more of the holes can extend through the support material.

As a further example, embodiments have been described in which the sheath of an implantable medical endoprostheses delivery system has one or more holes located therein, other embodiments are possible. As an example, a guide catheter (e.g., a guide catheter having the above-described multiple layer arrangement) can have one or more orifices located therein. The holes can be positioned toward the distal end of the guide catheter as described above.

Other embodiments are in the claims.

What is claimed is:

1. An implantable medical endoprosthesis delivery system, comprising:
   a catheter;
   a sheath at least partially surrounding the catheter, the catheter and the sheath being configured so that an implantable medical endoprosthesis can be disposed therebetween;
   a plurality of slots of material attached to the sheath; and
   a tip coupled to a distal end portion of the catheter, the tip having a head portion and a proximal portion, the head portion having a shaped surface including a plurality of proximally-extending projections that are in partial contact with a distal end surface of the sheath so that a plurality of longitudinal gaps are formed between the tip and the sheath such that there is fluid communication between an interior region of the sheath and an exterior region of the sheath through the longitudinal gaps; and
   wherein at least a section of the proximal portion is configured to be positioned within the slots of material.

2. The system of claim 1, wherein the shaped surface of the tip is a scalloped surface or a serrated surface.

3. The system of claim 1, wherein the proximal portion of the tip being attached to the catheter, the head portion of the tip comprising the shaped surface in partial contact with the distal end surface of the sheath.

4. The system of claim 1, wherein the implantable medical endoprosthesis capable of being disposed between the catheter and the sheath is a stent or a stent-graft.

5. The system of claim 1, further comprising the implantable medical endoprosthesis between the catheter and the sheath.

6. The system of claim 5, wherein the implantable medical endoprosthesis is a self-expanding implantable medical endoprosthesis.

7. The system of claim 5, wherein the implantable medical endoprosthesis is a balloon expandable implantable medical endoprosthesis.

8. An implantable medical endoprosthesis delivery system, comprising:
a catheter;
a sheath at least partially surrounding the catheter, the catheter and the sheath being configured so that an implantable medical endoprosthesis can be disposed therebetween;
a plurality of spacer members disposed along an interior wall surface of the sheath;
a tip coupled to a distal end portion of the catheter, the tip including a head portion and a proximal portion, the head portion including a surface cooperating with a distal end surface of the sheath to form a plurality of longitudinal gaps therebetween so that there is fluid communication between an interior region of the sheath and an exterior region of the sheath, wherein the surface of the tip comprises a plurality of proximally-extending projections that contact the distal end surface of the sheath at a plurality of circumferentially spaced regions; and
wherein the proximal portion of the tip is configured to be positioned within the spacer members.

9. The system of claim 8, wherein the surface of the tip is a scalloped surface or a serrated surface.

10. The system of claim 8, wherein the distal end surface of the sheath comprises a plurality of projections that contact the surface of the tip at a plurality of circumferentially spaced regions.

11. The system of claim 8, wherein the distal end surface of the sheath is a scalloped surface or a serrated surface.

12. The system of claim 8, wherein the implantable medical endoprosthesis capable of being disposed between the catheter and the sheath is a stent or a stent-graft.

13. The system of claim 8, further comprising the implantable medical endoprosthesis between the catheter and the sheath.

14. The system of claim 13, wherein the implantable medical endoprosthesis is a self-expanding implantable medical endoprosthesis.

15. The system of claim 13, wherein the implantable medical endoprosthesis is a balloon expandable implantable medical endoprosthesis.

16. The system of claim 8, wherein the proximal portion of the tip is attached to the catheter, the head portion of the tip comprising a proximal end surface that cooperates with the distal end surface of the sheath to form the plurality of gaps therebetween.

* * * * *

UNITED STATES PATENT AND TRADEMARK OFFICE
CERTIFICATE OF CORRECTION

PATENT NO. : 8,152,818 B2  
APPLICATION NO. : 11/838495  
DATED : April 10, 2012  
INVENTOR(S) : Richard C. Gunderson

Page 1 of 1

It is certified that error appears in the above-identified patent and that said Letters Patent is hereby corrected as shown below:

Column 8  
Line 17, delete "L", and insert therefor -- l --.  
Line 21, delete "T", and insert therefor -- t --.  
Line 22-23, delete "0.01 0", and insert therefor -- 0.010 --.

Column 9  
Line 60, delete "farther", and insert therefor -- further --.

Signed and Sealed this  
Twenty-ninth Day of May, 2012

David J. Kappos  
*Director of the United States Patent and Trademark Office*